(12) United States Patent
Liu

(10) Patent No.: US 11,439,187 B2
(45) Date of Patent: Sep. 13, 2022

(54) ELECTRONIC CIGARETTE

(71) Applicant: Tuanfang Liu, Shenzhen (CN)

(72) Inventor: Tuanfang Liu, Shenzhen (CN)

(*) Notice: Subject to any disclaimer, the term of this patent is extended or adjusted under 35 U.S.C. 154(b) by 301 days.

(21) Appl. No.: 16/899,605

(22) Filed: Jun. 12, 2020

(65) Prior Publication Data

US 2021/0093003 A1 Apr. 1, 2021

(30) Foreign Application Priority Data

Sep. 26, 2019 (CN) .......................... 201910919936.7
Sep. 26, 2019 (CN) .......................... 201921637885.0

(51) Int. Cl.
| | |
|---|---|
| *A24F 13/00* | (2006.01) |
| *A24F 17/00* | (2006.01) |
| *A24F 25/00* | (2006.01) |
| *A24F 40/42* | (2020.01) |
| *A24F 40/50* | (2020.01) |
| *A61M 15/00* | (2006.01) |
| *A24F 40/10* | (2020.01) |

(52) U.S. Cl.
CPC .............. *A24F 40/42* (2020.01); *A24F 40/10* (2020.01); *A24F 40/50* (2020.01); *A61M 15/0021* (2014.02); *A61M 2205/8206* (2013.01)

(58) Field of Classification Search
CPC .......... A24F 40/10; A24F 40/40; A24F 40/42; A24F 40/50; A61M 11/04; A61M 11/08; A61M 15/0021; A61M 15/06; A61M 2205/8206

See application file for complete search history.

(56) References Cited

U.S. PATENT DOCUMENTS

| | | | | |
|---|---|---|---|---|
| 11,071,328 | B2* | 7/2021 | Liu | ........................... A24F 7/02 |
| 11,089,821 | B2* | 8/2021 | Liu | ........................ A24F 40/40 |
| 2020/0113241 | A1* | 4/2020 | Liu | ........................ A24F 40/40 |
| 2021/0092998 | A1* | 4/2021 | Liu | ........................ A24F 40/10 |
| 2021/0153560 | A1* | 5/2021 | Liu | ........................ A24F 40/40 |
| 2021/0177058 | A1* | 6/2021 | Liu | ........................ A24F 40/46 |
| 2021/0195956 | A1* | 7/2021 | Han | ........................ A24F 40/42 |

* cited by examiner

*Primary Examiner* — Abdullah A Riyami
*Assistant Examiner* — Thang H Nguyen
(74) *Attorney, Agent, or Firm* — Matthias Scholl P.C.; Matthias Scholl

(57) ABSTRACT

An electronic cigarette including an atomization assembly and a base assembly. The atomization assembly includes a mouthpiece; a first seal ring; a first seal cover; an airflow regulation ring; a permanent seat; an O-shaped ring; an atomizer; a second seal ring; a funnel; a third seal ring; a spring; an e-liquid injector; a fourth seal ring; a second seal cover; a fifth seal ring; a press cover; a positive terminal; a first silicone pad; a connection cylinder; a cover plate; a sixth seal ring; an e-liquid tank; a seventh seal ring; a negative terminal; a first circular magnet; a first strip magnet; and a magnet cover. The battery assembly includes: a second circular magnet; a second strip magnet; a housing; a front cover plate; a press button; a back cover plate; a silicone plug; a battery; a control plate; a second silicone pad; and a LED cover.

1 Claim, 5 Drawing Sheets

ELECTRONIC CIGARETTE

CROSS-REFERENCE TO RELATED APPLICATIONS

Pursuant to 35 U.S.C. § 119 and the Paris Convention Treaty, this application claims foreign priority to Chinese Patent Application No. 201910919936.7 filed Sep. 26, 2019 and to Chinese Patent Application No. 201921637885.0 filed Sep. 26, 2019. The contents of all of the aforementioned applications, including any intervening amendments thereto, are incorporated herein by reference. Inquiries from the public to applicants or assignees concerning this document or the related applications should be directed to: Matthias Scholl Attn.: Dr. Matthias Scholl Esq., 245 First Street, 18th Floor, Cambridge, Mass. 02142.

BACKGROUND

The disclosure relates to an electronic cigarette.

Electronic cigarettes atomize nicotine-containing e-liquid.

Conventionally, the atomizer is fixedly connected to the mouthpiece assembly or the battery assembly of the electronic cigarette.

SUMMARY

The disclosure provides an electronic cigarette comprising an atomization assembly and a base assembly.

The atomization assembly comprises a mouthpiece; a first seal ring; a first seal cover; an airflow regulation ring; a permanent seat; an O-shaped ring; an atomizer; a second seal ring; a funnel; a third seal ring; a spring; an e-liquid injector; a fourth seal ring; a second seal cover; a fifth seal ring; a press cover; a positive terminal; a first silicone pad; a connection cylinder; a cover plate; a sixth seal ring; an e-liquid tank; a seventh seal ring; a negative terminal; a first circular magnet; a first strip magnet; and a magnet cover.

The battery assembly comprises: an end cover; a second circular magnet; a second strip magnet; a housing; a front cover plate; a press button; a back cover plate; a silicone plug; a pogo pin; a support; a battery; a control plate; a second silicone pad; and a LED cover.

The third seal ring and the spring are sequentially disposed on the funnel in that order; the funnel is disposed in the e-liquid injector; the fourth seal ring is disposed on the second seal cover; the second seal cover is directly connected to the funnel; the second seal ring encircles one end of the e-liquid injector; the e-liquid injector is disposed on the cover plate; the sixth seal ring encircles the cover plate; the cover plate is disposed on a first end face of the e-liquid tank; the seventh seal ring encircles the negative terminal; the negative terminal is disposed on a second end face of the e-liquid tank; the first circular magnet and the first strip magnet are disposed on two sides of the second end face of the e-liquid tank; the magnet cover is directly connected to the second end face of the e-liquid tank.

The positive terminal is disposed on the first silicone pad; the press cover covers the first silicone pad; the press cover and the first silicone pad are disposed in the connection cylinder; the positive terminal is connected to the fifth seal ring; the positive terminal and the fifth seal ring are disposed in an opening of the cover plate; the first seal ring and the O-shaped ring are disposed on two ends of the permanent seat, respectively; the airflow regulation ring encircles the permanent seat; the first seal cover is disposed in the permanent seat; the atomizer is in threaded connection to the permanent seat; the atomizer and the permanent seat are disposed in the connection cylinder; the mouthpiece is directly connected to the e-liquid tank.

The second circular magnet and the second strip magnet are fixed on the housing by the end cover; the pogo pin is disposed in a through hole of the support; and the silicone plug covers the pogo pin; the battery is connected to positive and negative terminals of the control plate; the second silicone pad and the LED cover are disposed on the control plate; the control plate is disposed in the support; the support is disposed in the housing; the press button is disposed on the housing; and the front cover plate and the back cover plate are disposed on two opposite sides, respectively.

The atomization assembly is connected to the base assembly through the attraction of the first circular/strip magnet and the second circular/strip magnet. The airflow regulation ring can adjust the vapor volume of the electronic cigarette. The air inlet and the e-liquid inlet are disposed on the top of the e-liquid tank, and the bottom of the e-liquid tank is airtight, thus preventing the leakage and permeation of the e-liquid into the battery assembly. Press the tunnel, and the e-liquid inlet of the e-liquid injector is exposed, and the e-liquid can flow into the e-liquid tank, Thereafter, the e-liquid inlet is sealed by the second seal cover, preventing the leakage of the e-liquid. The atomizer is in threaded connection to the permanent seat, which is convenient to replacing the atomizer.

DETAILED DESCRIPTION

To further illustrate, embodiments detailing an electronic cigarette are described below. It should be noted that the following embodiments are intended to describe and not to limit the disclosure.

Figure 1:
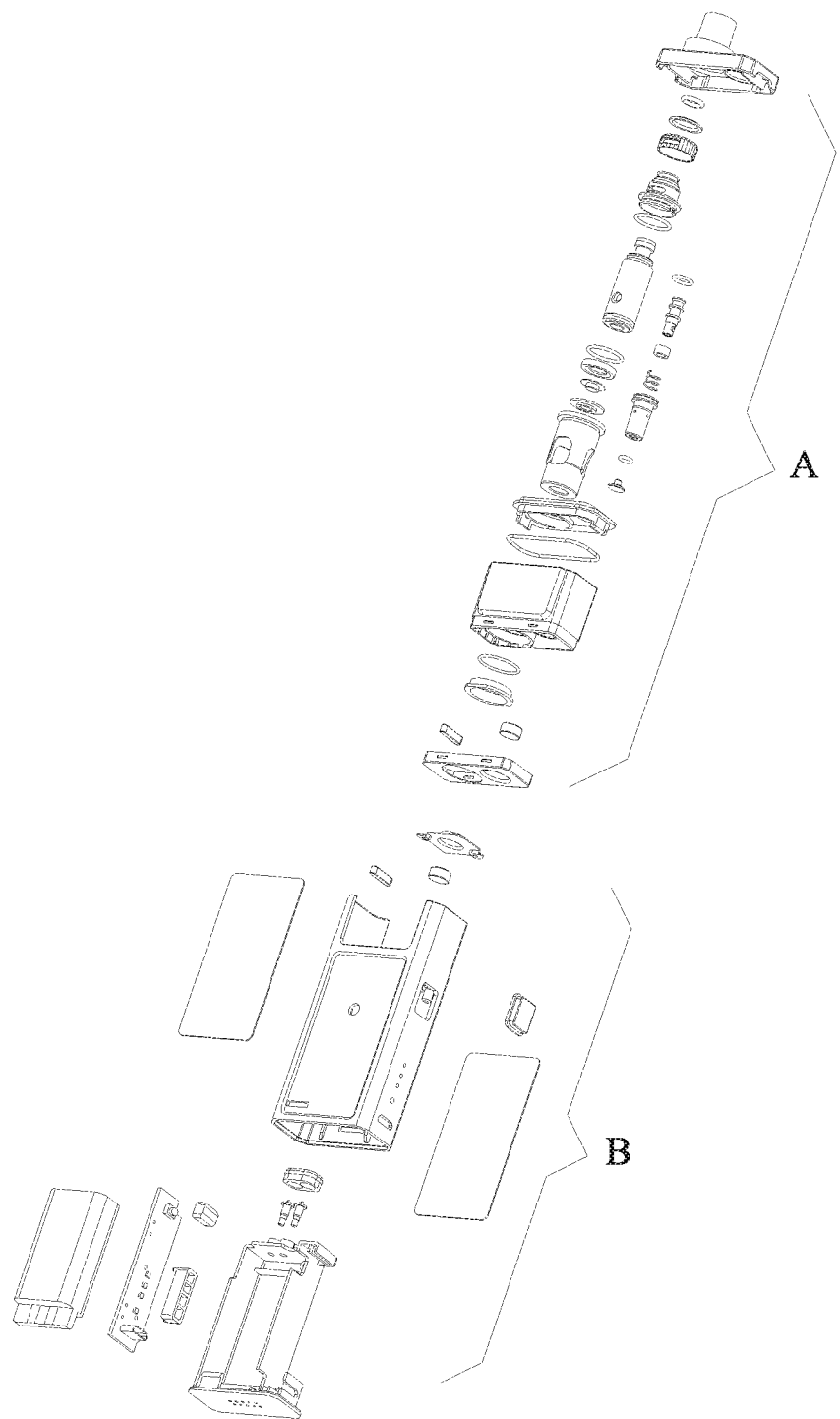
FIG. 1 is an exploded view of an electronic cigarette according to one embodiment of the disclosure.
Figure 2:
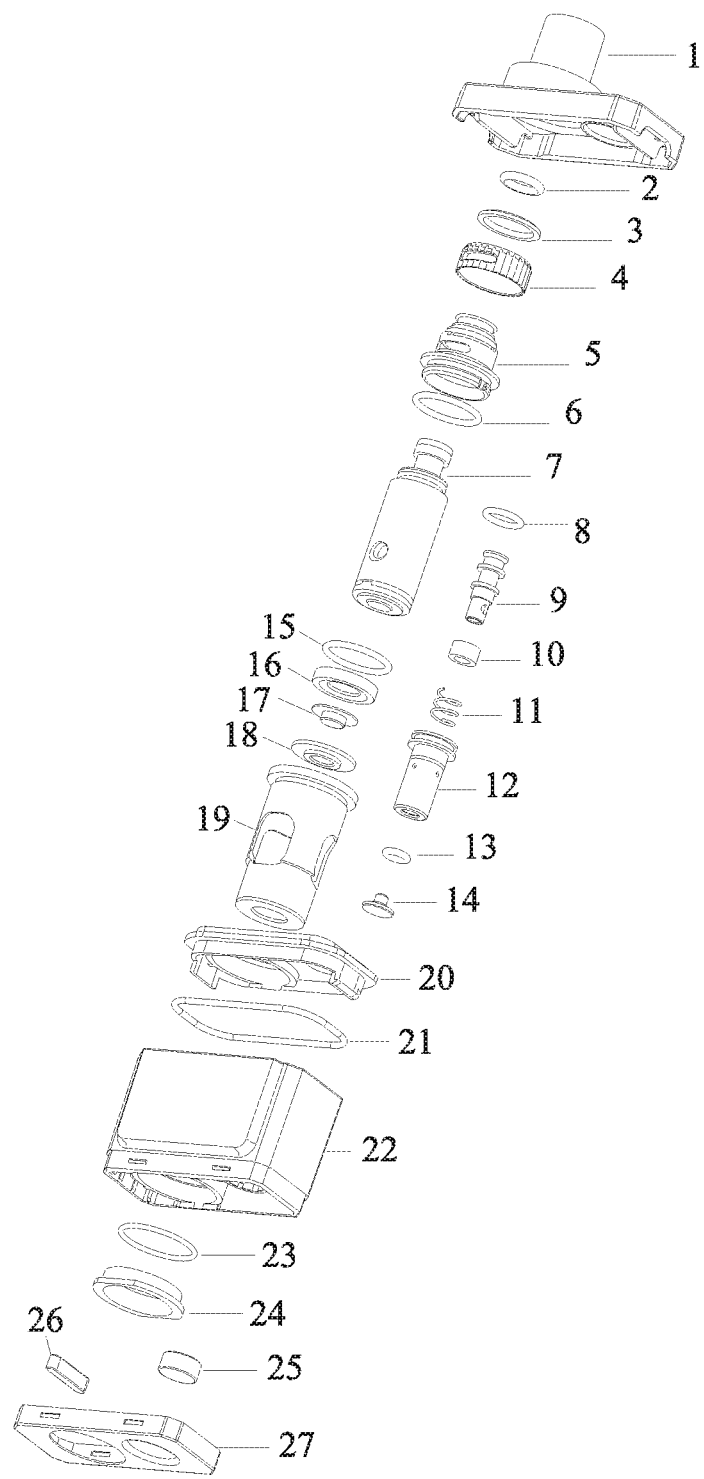
FIG. 2 is an exploded view of an atomization assembly of an electronic cigarette according to one embodiment of the disclosure.
Figure 3:
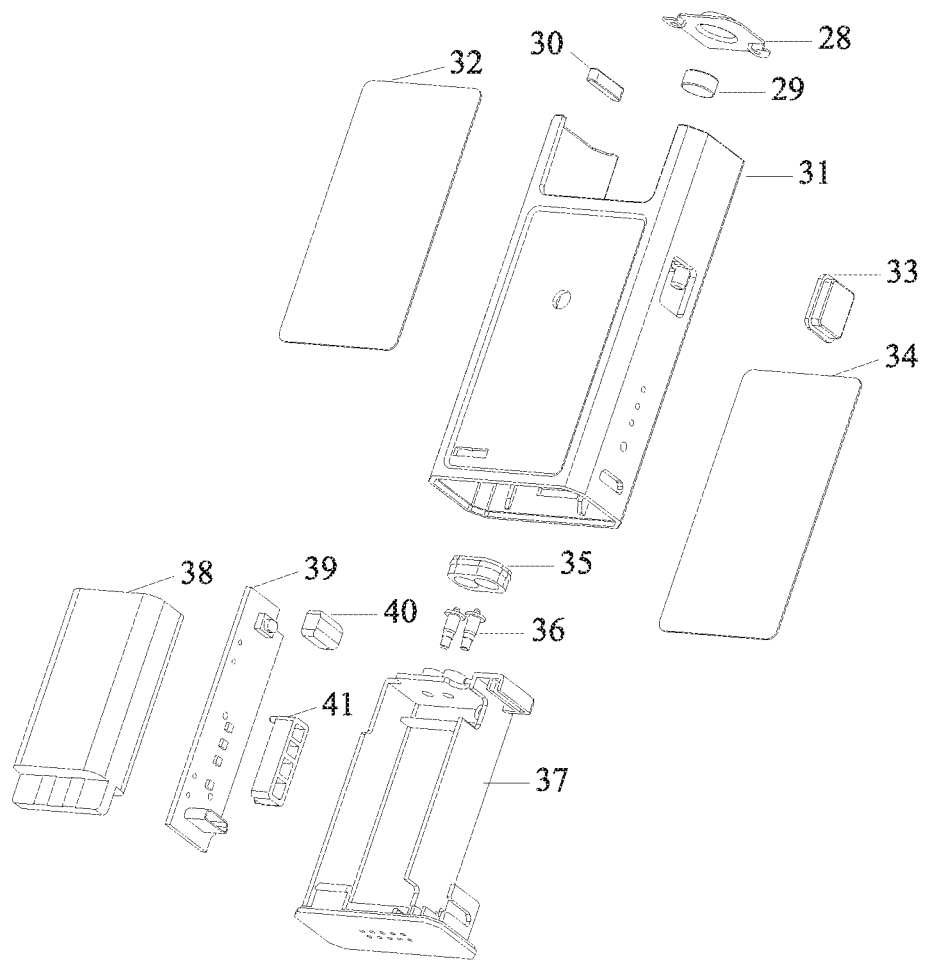
FIG. 3 is an exploded view of a base assembly of an electronic cigarette according to one embodiment of the disclosure.
Figure 4:
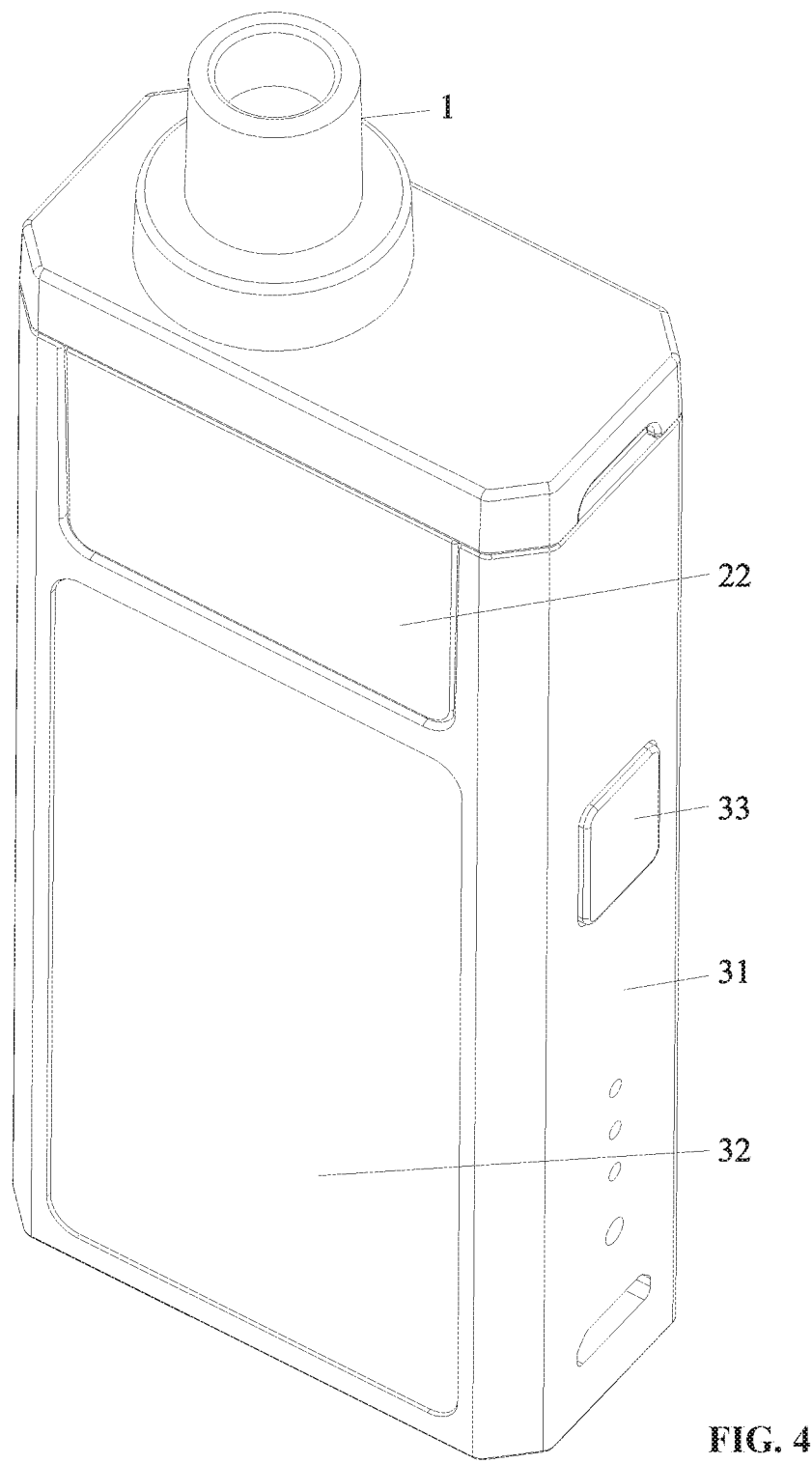
FIG. 4 is a front view of an electronic cigarette according to one embodiment of the disclosure.
Figure 5:
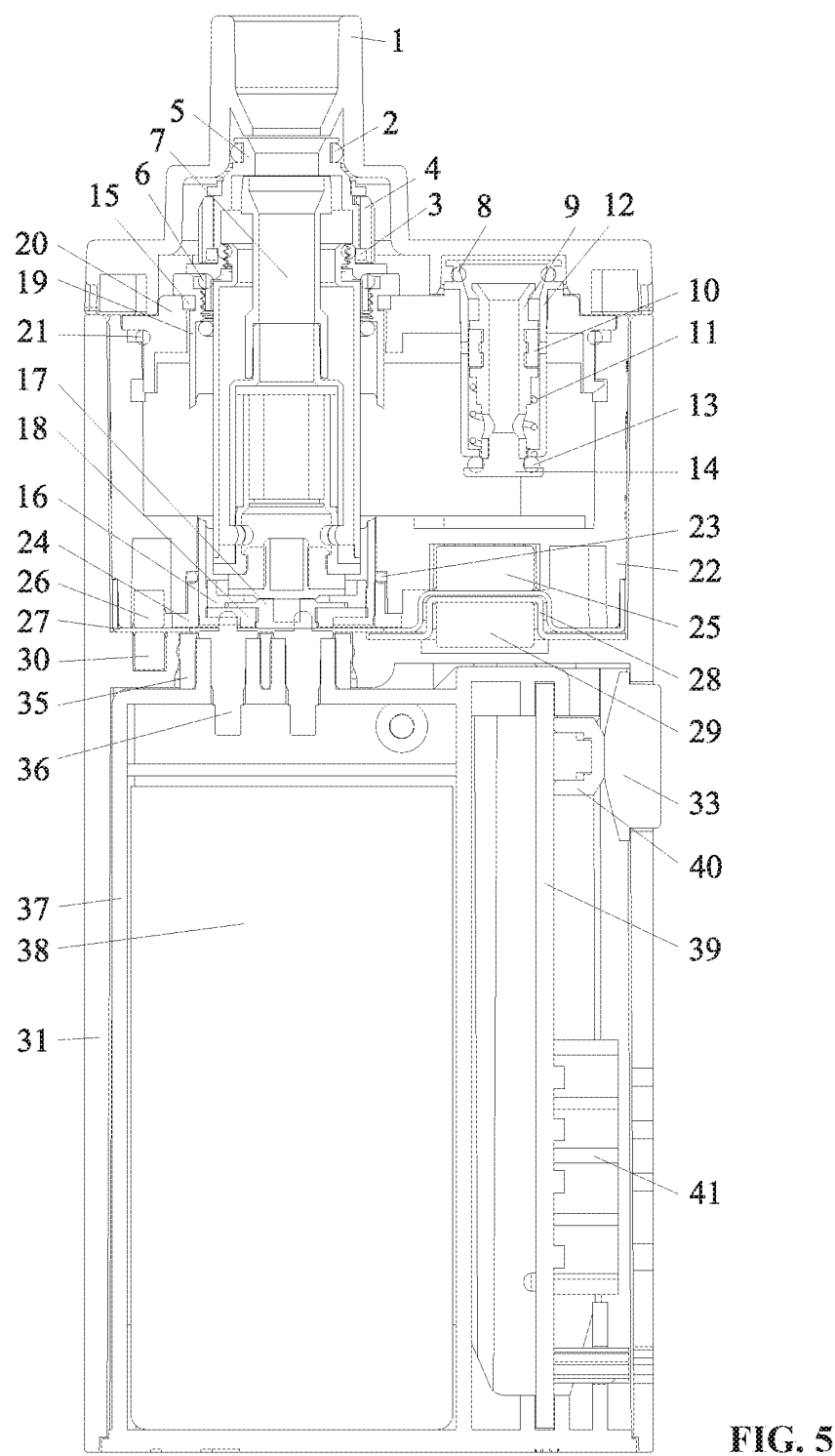
FIG. 5 is a sectional view of an electronic cigarette according to one embodiment of the disclosure.

As shown in FIGS. 1-5, an electronic cigarette comprises an atomization assembly A and a battery assembly B. The atomization assembly comprises: a mouthpiece 1; a first seal ring 2; a first seal cover 3; an airflow regulation ring 4; a permanent seat 5; an O-shaped ring 6; an atomizer 7; a second seal ring 8; a funnel 9; a third seal ring 10; a spring 11; an e-liquid injector 12; a fourth seal ring 13; a second seal cover 14; a fifth seal ring 15; a press cover 16; a positive terminal 17; a first silicone pad 18; a connection cylinder 19; a cover plate 20; a sixth seal ring 21; an e-liquid tank 22; a seventh seal ring 23; a negative terminal 24; a first circular magnet 25; a first strip magnet 26; and a magnet cover 27.

The third seal ring 10 and the spring 11 are sequentially disposed on the funnel 9 in that order; the funnel 9 is disposed in the e-liquid injector 12; the fourth seal ring 13 is disposed on the second seal cover 14; the second seal cover 14 is directly connected to the funnel 9; the second seal ring 8 encircles one end of the e-liquid injector 12; the e-liquid injector 12 is disposed on the cover plate 20.

The sixth seal ring 21 encircles the cover plate 20; the cover plate 20 is disposed on a first end face of the e-liquid tank 22; the seventh seal ring 23 encircles the negative terminal 24; the negative terminal 24 is disposed on a second end face of the e-liquid tank 22; the first circular magnet 25 and the first strip magnet 26 are disposed on two sides of the second end face of the e-liquid tank 22; the magnet cover 27 is directly connected to the second end face of the e-liquid tank 22.

The positive terminal 17 is disposed on the first silicone pad 18; the press cover 16 covers the first silicone pad 18; the press cover 16 and the first silicone pad 18 are disposed in the connection cylinder 19; the positive terminal 17 is connected to the fifth seal ring 15; the positive terminal 17 and the fifth seal ring 15 are disposed in an opening of the cover plate 20; the first seal ring 2 and the O-shaped ring 6 are disposed on two ends of the permanent seat 5, respectively; the airflow regulation ring 4 encircles the permanent seat 5; the first seal cover 3 is disposed in the permanent seat 5; the atomizer 7 is in threaded connection to the permanent seat 5; the atomizer 7 and the permanent seat 5 are disposed in the connection cylinder 19; the mouthpiece 1 is directly connected to the e-liquid tank 22.

The airflow regulation ring 4 can adjust the vapor volume of the electronic cigarette, The air inlet and the e-liquid inlet are disposed on the top of the e-liquid tank 22, and the bottom of the e-liquid tank 22 is airtight, thus preventing the leakage and permeation of the e-liquid into the battery assembly. Press the tunnel 9, and the e-liquid inlet of the e-liquid injector 12 is exposed, and the e-liquid can flow into the e-liquid tank 22. Thereafter, the e-liquid inlet is sealed by the second seal cover 14, preventing the leakage of the e-liquid. The atomizer 7 is in threaded connection to the permanent seat 5, thus simplifying the replacement of the atomizer.

The battery assembly comprises an end cover 28; a second circular magnet 29; a second strip magnet 30; a housing 31; a front cover plate 32; a press button 33; a back cover plate 34; a silicone plug 35; a pogo pin 36; a support 37; a battery 38; a control plate 39; a second silicone pad 40; and a LED cover 41.

The second circular magnet 29 and the second strip magnet 30 are fixed on the housing 31 by the end cover 28; the pogo pin 36 is disposed in a through hole of the support 37; and the silicone plug 35 covers the pogo pin 36.

The battery 38 is connected to positive and negative terminals of the control plate 39; the second silicone pad 40 and the LED cover 41 are disposed on the control plate 39; the control plate 39 is disposed in the support 37; the support 37 is disposed in the housing 31; the press button 33 is disposed on the housing 31; and the front cover plate 32 and the back cover plate 34 are disposed on two opposite sides, respectively.

It will be obvious to those skilled in the art that changes and modifications may be made, and therefore, the aim in the appended claims is to cover all such changes and modifications.

What is claimed is:

1. A device, comprising: an atomization assembly and a battery assembly; the atomization assembly being disposed on the battery assembly;
    the atomization assembly comprising:
        1) a mouthpiece;
        2) a first seal ring;
        3) a first seal cover;
        4) an airflow regulation ring;
        5) a permanent seat;
        6) an O-shaped ring;
        7) an atomizer;
        8) a second seal ring;
        9) a funnel;
        10) a third seal ring;
        11) a spring;
        12) an e-liquid injector;
        13) a fourth seal ring;
        14) a second seal cover;
        15) a fifth seal ring;
        16) a press cover;
        17) a positive terminal;
        18) a first silicone pad;
        19) a connection cylinder;
        20) a cover plate;
        21) a sixth seal ring;
        22) an e-liquid tank;
        23) a seventh seal ring;
        24) a negative terminal;
        25) a first circular magnet;
        26) a first strip magnet; and
        27) a magnet cover;
    the battery assembly comprising:
        28) an end cover;
        29) a second circular magnet;
        30) a second strip magnet;
        31) a housing;
        32) a front cover plate;
        33) a press button;
        34) a back cover plate;
        35) a silicone plug;
        36) a pogo pin;
        37) a support;
        38) a battery;
        39) a control plate;
        40) a second silicone pad; and
        41) a LED cover;
    wherein:
        the third seal ring and the spring are sequentially disposed on the funnel in that order; the funnel is disposed in the e-liquid injector;
        the fourth seal ring is disposed on the second seal cover; the second seal cover is directly connected to the funnel; the second seal ring encircles one end of the e-liquid injector; the e-liquid injector is disposed on the cover plate;
        the sixth seal ring encircles the cover plate; the cover plate is disposed on a first end face of the e-liquid tank; the seventh seal ring encircles the negative terminal; the negative terminal is disposed on a second end face of the e-liquid tank; the first circular magnet and the first strip magnet are disposed on two sides of the second end face of the e-liquid tank; the magnet cover is directly connected to the second end face of the e-liquid tank;
        the positive terminal is disposed on the first silicone pad; the press cover covers the first silicone pad; the press cover and the first silicone pad are disposed in the connection cylinder; the positive terminal is directly connected to the fifth seal ring; the positive terminal and the fifth seal ring are disposed in an opening of the cover plate;
        the first seal ring and the O-shaped ring are disposed on two ends of the permanent seat, respectively; the airflow regulation ring encircles the permanent seat;

the first seal cover is disposed in the permanent seat; the atomizer is in threaded connection to the permanent seat; the atomizer and the permanent seat are disposed in the connection cylinder; the mouthpiece is directly connected to the e-liquid tank;

the second circular magnet and the second strip magnet are fixed on the housing by the end cover; the pogo pin is disposed in a through hole of the support; and the silicone plug covers the pogo pin; and the battery is connected to positive and negative terminals of the control plate; the second silicone pad and the LED cover are disposed on the control plate; the control plate is disposed in the support; the support is disposed in the housing; the press button is disposed on the housing; and the front cover plate and the back cover plate are disposed on two opposite sides, respectively.

\* \* \* \* \*